(12) United States Patent
Takase et al.

(10) Patent No.: US 7,901,699 B2
(45) Date of Patent: Mar. 8, 2011

(54) COSMETIC COMPOSITION AND COSMETICS

(75) Inventors: Yoshihiko Takase, Mie-ken (JP); Kazuhito Uchida, Mie-ken (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 11/571,299

(22) PCT Filed: Jun. 29, 2005

(86) PCT No.: PCT/JP2005/011957
§ 371 (c)(1), (2), (4) Date: Dec. 27, 2006

(87) PCT Pub. No.: WO2006/003941
PCT Pub. Date: Jan. 12, 2006

(65) Prior Publication Data
US 2007/0248631 A1    Oct. 25, 2007

(30) Foreign Application Priority Data

Jun. 30, 2004 (JP) ................. 2004-194631
Jun. 29, 2005 (JP) ................. 2005-011957

(51) Int. Cl.
*A61K 8/02* (2006.01)
*A61K 8/31* (2006.01)

(52) U.S. Cl. ..................... 424/401; 424/70.31

(58) Field of Classification Search ........... None
See application file for complete search history.

(56) References Cited

U.S. PATENT DOCUMENTS

| | | | |
|---|---|---|---|
| 3,926,840 A * | 12/1975 | Wendler et al. ........... | 516/28 |
| 3,928,212 A * | 12/1975 | Goto et al. ............... | 252/8.63 |
| 4,233,164 A * | 11/1980 | Davis ..................... | 8/137 |
| 4,420,410 A * | 12/1983 | Huttinger ................ | 510/427 |
| 5,145,898 A * | 9/1992 | Narula et al. ............ | 524/310 |
| 6,346,507 B1 * | 2/2002 | Watanabe et al. ......... | 510/343 |
| 6,667,043 B1 | 12/2003 | Podubrin et al. | |
| 7,282,520 B2 * | 10/2007 | Yokomaku et al. ....... | 514/532 |
| 2004/0013634 A1 * | 1/2004 | Novikov et al. .......... | 424/73 |

FOREIGN PATENT DOCUMENTS

| | | |
|---|---|---|
| CN | 1134816 A | 11/1996 |
| DE | 19604744 A1 | 8/1997 |
| DE | 19827662 A1 | 12/1999 |
| DE | 10252235 A1 | 5/2004 |
| JP | 56097210 A | 8/1981 |
| JP | 62-108806 | 5/1987 |
| JP | 8-40828 | 2/1996 |
| JP | 11-139934 | 5/1999 |
| JP | 2000-327529 | 11/2000 |
| JP | 2001025654 A * | 1/2001 |
| JP | 2003-95919 | 4/2003 |
| JP | 2003-160436 | 6/2003 |
| JP | 2004-175736 | 6/2004 |
| JP | 2005-162691 | 6/2005 |
| WO | 99/66884 A1 | 12/1999 |
| WO | WO 0123515 A1 * | 4/2001 |
| WO | WO 03/026598 A1 * | 4/2003 |
| WO | 03/051319 A1 | 6/2003 |

OTHER PUBLICATIONS

Jack H. Schulman et al; Mechanism of Formation and Structure of Micro Emulsions by Electron Microscopy; J. Phys. Chem.; vol. 63; Jun. 8, 1959.
European Patent Office, EP Search Report received in corresponding EP Application Serial No. 05755808.2-2108 dated Aug. 25, 2010, 3 pages.
Chinese Patent Office, Chinese Office Action in counterpart CN Application Serial No. 200580021340.1 issued Sep. 18, 2009, 11 pages.

* cited by examiner

*Primary Examiner* — Sreeni Padmanabhan
*Assistant Examiner* — Layla Soroush
(74) *Attorney, Agent, or Firm* — Wood, Herron & Evans, LLP

(57) ABSTRACT

Liquid cleansing oils capable of mixing well with old makeup and being easily rinsed off with water have come into the mainstream in recent years. An object of the present invention is to provide a cosmetic composition which easily mixes with old makeup, enables the old makeup to be lifted off rapidly, demonstrates superior cleansing strength even if the skin is wet, demonstrates satisfactory ease of rinsing, has a satisfactory feel during use without leaving an oily sensation after washing, and demonstrates superior moisture dispersivity. The present invention achieves this object by comprising a nonionic surfactant and a polyvalent alcohol fatty acid ester of a fatty acid having 6 to 12 carbon atoms and a polyvalent alcohol having 2 to 4 hydroxyl groups; wherein, the total amount of monoester and diester in the ester is 50% or more, and the weight ratio of monoester to diester is 4 or less.

8 Claims, 4 Drawing Sheets

FIG. 1A

|  | Examples | | | | | | | | | | | | |
|---|---|---|---|---|---|---|---|---|---|---|---|---|---|
|  | 1 | 2 | 3 | 4 | 5 | 6 | 7 | 8 | 9 | 10 | 11 | 12 | 13 |
| Decaglycerin monoisostearate (ring form: 8.6%) |  |  | 15 | 10 |  | 5 |  |  |  |  |  |  |  |
| Decaglycerin trilaurate (ring form: 18.4%) |  | 20 |  |  | 10 | 15 |  |  |  |  |  | 10 |  |
| Decaglycerin dioleate (ring form: 8.0%) | 20 |  |  | 10 | 10 |  | 20 |  |  |  |  | 10 |  |
| Decaglycerin dioleate (ring form: 26.6%) |  |  |  |  |  |  |  |  |  |  |  |  | 20 |
| Decaglycerin dioleate (ring form: 42.4%) |  |  |  |  |  |  |  |  | 20 |  |  |  |  |
| Polyoxyethylene hydrogenated castor oil (10EO) |  |  |  |  |  |  |  | 10 |  |  |  |  |  |
| Polyoxyethylene sorbitan monooleate (20EO) |  |  |  |  |  |  |  |  |  |  | 5 |  |  |
| Polyoxyethylene oleyl ether (10EO) |  |  |  |  |  |  |  |  |  | 5 | 25 |  |  |
| Glyceryl caprylate (ME/DE=4, ME+DE = 90%) |  | 10 |  |  |  |  |  | 5 |  | 5 | 10 |  |  |
| Glyceryl caprylate (ME/DE=1.5, ME+DE=87%) | 10 |  |  |  |  | 5 |  | 5 | 10 |  |  |  | 10 |
| Glyceryl caprylate (ME/DE=0.42, ME+DE=78%) |  |  | 5 |  |  |  |  |  |  |  |  |  |  |
| Glyceryl caprylate (ME/DE=9, ME+DE=92%) |  |  |  |  |  |  |  |  |  |  |  |  |  |
| Glyceryl caprate (ME/DE=0.25, ME+DE=73%) |  |  |  | 10 |  |  |  |  |  |  |  |  |  |
| Diglyceryl caprylate (ME/DE=2.33, ME+DE=71%) |  |  |  |  | 10 |  |  |  |  |  |  |  |  |
| Diglyceryl caprylate (ME/DE=0, ME+DE=57%) |  |  |  |  |  |  |  |  |  |  |  | 10 |  |
| Diglyceryl caprate (ME/DE=0.67, ME+DE=90%) |  |  |  |  |  | 5 |  |  |  |  |  |  |  |
| Diglyceryl caprate (ME/DE=9, ME+DE=90%) |  |  |  |  |  |  |  |  |  |  |  |  |  |
| Sorbitan laurate (ME/DE=2.33, ME+DE=74%) |  |  |  |  |  |  | 5 |  |  |  |  |  |  |
| Sorbitan caprate (ME/DE=0.25, ME+DE=55%) |  |  |  |  |  |  |  |  |  |  | 5 |  |  |
| Pentaerythritol laurate (ME/DE=1, ME+DE=90%) |  |  |  |  |  |  |  |  |  |  |  | 5 |  |
| Glyceryl caprylate (ME/DE=0.25, ME+DE=40%) |  |  |  |  |  |  |  |  |  |  |  |  |  |
| Sorbitan caprate (ME/DE=4, ME+DE=34%) |  |  |  |  |  |  |  |  |  |  |  |  |  |
| Cyclomethicone | 10 |  |  |  |  |  |  | 10 | 10 |  |  |  | 10 |
| Octyl palmitate | 10 | 50 |  | 70 | 30 | 30 | 65 | 50 | 10 |  | 20 | 30 | 10 |
| Liquid paraffin | 50 | 10 | 10 |  | 5 | 40 |  | 10 | 50 | 20 |  | 5 | 50 |

FIG. 1B

| | | | | | | | | | | | | | |
|---|---|---|---|---|---|---|---|---|---|---|---|---|---|
| Isopropyl myristate | | | 70 | | 30 | | 10 | | | 30 | 10 | 30 | |
| Olive oil | | 10 | | | 5 | | | 10 | | 30 | | 5 | |
| Water | | | | | | | | | | | 30 | | |
| 1 | Solubili- zation rate (microemulsion formation) | 76 | 56 | 72 | 50 | 74 | 68 | 70 | 29 | 37 | 30 | 18 | 50 | 55 |
| 2 | Cleansing strength (dry hands) | A | A | A | A | A | A | A | A | A | A | A | A | A |
| 3 | Cleansing strength (wet hands) | A | A | A | A | A | A | A | B | B | B | B | A | A |
| 4 | Mixing with old makeup | A | A | A | A | A | A | A | B | A | B | B | A | A |
| | Rinsing ease | A | B | A | B | A | A | A | B | B | B | B | B | A |
| | Lack of oily sensation | A | A | A | A | A | A | A | B | B | B | B | A | A |

Ring form: Percentage of ring forms in polyglycerin as measured by LC/MS.

ME/DE: Weight ratio of monoester to diester

5    ME+DE: Total amount of monoester and diester

FIG. 2A

|  | Comparative Examples |||||||||| 
|---|---|---|---|---|---|---|---|---|---|---|
|  | 1 | 2 | 3 | 4 | 5 | 6 | 7 | 8 | 9 | 10 |
| Decaglycerin monoisostearate (ring form: 8.6%) | 30 |  |  |  | 20 |  |  |  | 20 |  |
| Decaglycerin trilaurate (ring form: 18.4%) |  | 30 |  |  |  |  |  |  |  | 20 |
| Decaglycerin dioleate (ring form: 8.0%) |  |  | 10 |  |  | 20 |  |  |  |  |
| Decaglycerin dioleate (ring form: 26.6%) |  |  |  |  |  |  |  |  |  |  |
| Decaglycerin dioleate (ring form: 42.4%) |  |  |  |  |  |  |  |  |  |  |
| Polyoxyethylene hydrogenated castor oil (10EO) |  |  | 10 |  |  |  |  |  |  |  |
| Polyoxyethylene sorbitan monooleate (20EO) |  |  |  | 20 |  |  | 10 |  |  |  |
| Polyoxyethylene oleyl ether (10EO) |  |  |  |  |  |  | 10 | 30 |  |  |
| Glyceryl caprylate (ME/DE=4, ME+DE = 90%) |  |  |  |  |  |  |  |  |  |  |
| Glyceryl caprylate (ME/DE=1.5, ME+DE=87%) |  |  |  |  |  |  |  |  |  |  |
| Glyceryl caprylate (ME/DE=0.42, ME+DE=78%) |  |  |  |  |  |  |  |  |  |  |
| Glyceryl caprylate (ME/DE=9, ME+DE=92%) |  |  |  |  | 10 |  |  |  |  |  |
| Glyceryl caprate (ME/DE=0.25, ME+DE=73%) |  |  |  |  |  |  |  |  |  |  |
| Diglyceryl caprylate (ME/DE=2.33, ME+DE=71%) |  |  |  |  |  |  |  |  |  |  |
| Diglyceryl caprylate (ME/DE=0, ME+DE=57%) |  |  |  |  |  |  |  |  |  |  |
| Diglyceryl caprate (ME/DE=0.67, ME+DE=90%) |  |  |  |  |  |  |  |  |  |  |
| Diglyceryl caprate (ME/DE=9, ME+DE=90%) |  |  |  |  |  | 10 |  |  |  |  |
| Sorbitan laurate (ME/DE=2.33, ME+DE=74%) |  |  |  |  |  |  |  |  |  |  |
| Sorbitan caprate (ME/DE=0.25, ME+DE=55%) |  |  |  |  |  |  |  |  |  |  |

FIG. 2B

| | | | | | | | | | | |
|---|---|---|---|---|---|---|---|---|---|---|
| Pentaerythritol laurate (ME/DE=1, ME+DE=90%) | | | | | | | | | | |
| Glyceryl caprylate (ME/DE=0.25, ME+DE=40%) | | | | | | | | | 10 | |
| Sorbitan caprate (ME/DE=4, ME+DE=34%) | | | | | | | | | | 10 |
| Cyclomethicone | | | | | 10 | | | | 10 | 10 |
| Octyl palmitate | 50 | 70 | | 40 | 10 | 10 | 20 | | 10 | 10 |
| Liquid paraffin | 10 | | 10 | 5 | 70 | 50 | 70 | | 50 | 50 |
| Isopropyl myristate | | | 70 | 30 | | | | 10 | | |
| Olive oil | 10 | | | 5 | | | | | | |
| Water | | | | | | | | 40 | | |
| 1 Solubilization rate (microemulsion formation) | 5 | 4 | 3 | 2 | 8 | 9 | 3 | 3 | 8 | 9 |
| 2 Cleansing strength (dry hands) | C | B | B | C | B | C | D | D | C | C |
| 3 Cleansing strength (wet hands) | D | D | D | D | D | D | D | D | D | D |
| 4 Mixing with old makeup | C | B | B | B | B | C | D | D | B | B |
| Rinsing ease | C | B | B | B | B | B | D | D | C | C |
| Lack of oily sensation | C | B | C | C | C | B | C | D | C | C |

Ring form: Percentage of ring forms in polyglycerin as measured by LC/MS.

ME/DE: Weight ratio of monoester to diester

ME+DE: Total amount of monoester and diester

COSMETIC COMPOSITION AND COSMETICS

FIELD OF THE INVENTION

The present invention relates to a cosmetic composition comprising a nonionic surfactant and a polyvalent alcohol fatty acid ester of a fatty acid having 6 to 12 carbon atoms and a polyvalent alcohol having 2 to 4 hydroxyl groups, the total amount of monoester and diester in the ester being 50% or more, and the weight ratio of monoester to diester being 4 or less, and more particularly, to a cosmetic composition capable of being used in basic cosmetics such as cleansing cosmetics such as a cleansing oil suitable for hard makeup having satisfactory mixing with makeup regardless of whether or not skin is wet, bathing cosmetics such as a bath oil which enhances bathing effects by adding to bath water, toiletry products such as scalp cleansers used prior to shampooing, and emulsified cosmetics.

Priority is claimed on Japanese Patent Application No. 2004-194631, filed on Jun. 30, 2004, the content of which is incorporated herein by reference.

BACKGROUND ART

In the field of cosmetics, cleansing cosmetics for removing makeup are in the form of creams, milky lotions and liquids, and are available in types consisting of emulsions, oils and aqueous types which are used corresponding to their respective ease of use. However, aqueous types, which contain no or very little oil, had the problem of having weak cleansing strength despite leaving little oily feeling after cleansing. Consequently, liquid cleansing oils have come into the mainstream in recent years which are capable of easily mixing into old makeup and which can be easily rinsed off with water. Cleansing oils are self-emulsifying oily liquid compositions comprised of a mixture of an oily component and a surfactant. These products have the property of rapidly undergoing a phase inversion when contacted with water, and first involve the migration of old makeup into an oily component as a result of mixing between the cleansing cosmetic and makeup, followed by the formation of an oil-in-water emulsion by the oily component containing old makeup as a result of contact with water, and finally removing the makeup by rinsing with water (see, for example, patent document 1). Since this type of self-emulsifying composition forms an emulsion simultaneous to contact with water, cleansing strength and feel during use are poor when the skin is wet, thereby making this unsuitable for use in the bathroom. On the other hand, a technology has also been disclosed for demonstrating cleansing strength even when in contact with water by containing a polyvalent alcohol or water in addition to an oily component and a surfactant (see, for example, patent document 2). However, since it is necessary for this type of cleansing composition to incorporate numerous types and large amounts of components other than oil, it had the problem of decreased cleansing strength as compared with typical cleansing oils.

Next, bathing cosmetics prevent damaged skin, cracked skin and chapped skin, and are frequently used during bathing to improve skin condition. Examples of the forms of bathing cosmetics include bath salts, bath oils and herbs. In particular, self-emulsifying, oily bath oil type products comprised of a mixture of an oily component and a surfactant self-emulsify in hot water when placed in a bath, resulting in the oily component in the form of fine particles being uniformly dispersed in the bathwater, and making it possible for the oily component to demonstrate various type of inherent ameliorative effects possessed thereby such as that of an emollient, moisture retention, anti-inflammatory effects and hot bathing effects. However, since conventional self-emulsifying oily bathing cosmetics comprised of a mixture of an oily component and a surfactant have inadequate dispersivity in hot water, they had the problem of remaining in the form of the bathing cosmetic and being suspended in the water as a result of self-emulsification not occurring. As a result, in addition to having a poor feel on the skin after bathing in the form of unpleasantness during bathing and a damp feeling on the skin, there was also the problem of the bathing cosmetic adhering to the walls of the bathtub.

The formation of a microemulsion during the process of adding water is effective for these problems. Microemulsions are systems in which a greater amount of oil (or water) is solubilized than ordinary micelle solutions (or reverse micelle oily solutions), and are anisotropic solutions having a clear to blue appearance. Similar to ordinary macroemulsions, microemulsions exist in one of two types consisting of oil-in-water (O/W) and water-in-oil (W/O) types, while there are also microemulsions in which an oily phase and aqueous phase, in which large amounts of water and oil are solubilized, are continuous (bicontinuous). Conventional liquid oily cleansing cosmetics and oily bathing cosmetics are either surfactant oily solutions comprising a mixture of a surfactant and an oil, or reverse micelle oily solutions to which an extremely small amount of water has been added, and since these oily solutions are only capable of solubilizing small amounts of water, they undergo phase separation and form a cloudy emulsion when the solubilization limit is exceeded. Consequently, they emulsify instantaneously in the case the hands and so forth are wet, resulting in decreased cleansing strength.

Microemulsions are known to be obtained by adding an auxiliary surfactant in the form of an intermediate alcohol having 5 to 10 carbon atoms to three components consisting of water, surfactant and oil (see, for example, non-patent document 1). However, these intermediate alcohols have been unable to be used in cosmetics or pharmaceuticals due to skin irritation and other problems with safety.

[patent document 1] Japanese Examined Patent Application, Second Publication No. H6-99275
[patent document 2] Japanese Unexamined Patent Application, First Publication No. 2000-327529
[non-patent document 1] J. H. Schulman, W. Stoeckenius and L. M. Prince: J. Phys. Chem., 63, 1677 (1959)

DISCLOSURE OF THE INVENTION

Problems to be Solved by the Invention

An object of the present invention is to provide a cosmetic composition having satisfactory mixing with old makeup, rapidly lifts off old makeup from the skin, demonstrates superior cleansing strength even if the skin is wet, has satisfactory rinsing, has a satisfactory feel during use without causing an oily sensation to remain after washing, has a high degree of transparency, and has superior moisture dispersivity.

Means for Solving the Problem

The inventors of the present invention found that a cosmetic composition combining the use of a nonionic surfactant and a specific polyvalent alcohol fatty acid ester can be used in, for example, cleansing cosmetics having superior cleansing strength even if the skin is wet while also demonstrating satisfactory mixing with old makeup, and in bathing cosmetics having superior moisture dispersivity and satisfactory self-emulsification, as a result of forming a microemulsion in the presence of water. Although a polyvalent alcohol fatty acid ester of a fatty acid having 6 to 12 carbon atoms and a polyvalent alcohol having 2 to 4 hydroxyl groups are satisfactory surfactants in terms of safety as is exemplified by fatty acid esters such as glycerin, diglycerin and propylene glycol which are permitted for use as food additives, in the present invention, by using a polyvalent alcohol fatty acid ester as an auxiliary surfactant, a microemulsion is formed which solubilizes a large amount of water. Since this microemulsion is of the water-in-oil type in which the continuous phase is oil and thus this microemulsion is mixed well with old makeup and large amounts of water is solubilized, in the case of incorporating an ester of a fatty acid having 6 to 12 carbon atoms and a polyvalent alcohol having 2 to 4 hydroxyl groups in which the total amount of monoester and diester in the ester is 50% or more and the weight ratio of monoester to diester is 4 or less, the microemulsion was determined to be able to be used without impairing function even if the hands are wet. In addition, since surface tension of the oil/water interface decreases due to the formation of a microemulsion in the process of adding water, namely in the washing process, a fine emulsion is formed as a result of emulsification occurring easily following the addition of a large amount of water. Consequently, cleansing performance and moisture dispersivity were drastically improved as compared with conventional cleansing cosmetics and bathing cosmetics.

Namely, the present invention provides a cosmetic composition comprising: a nonionic surfactant and a polyvalent alcohol fatty acid ester of a fatty acid having 6 to 12 carbon atoms and a polyvalent alcohol having 2 to 4 hydroxyl groups; wherein, the total amount of monoester and diester in the ester is 50% or more, and the weight ratio of monoester to diester is 4 or less.

Effects of the Invention

A cosmetic composition of the present invention comprising a nonionic surfactant and a polyvalent alcohol fatty acid ester of a fatty acid having 6 to 12 carbon atoms and a polyvalent alcohol having 2 to 4 hydroxyl groups, wherein the total amount of monoester and diester in the ester is 50% or more, and the weight ratio of monoester to diester is 4 or less, can be used in cleansing cosmetics having superior cleansing strength even if the skin is wet while also demonstrating satisfactory mixing with old makeup, and in bathing cosmetics having superior moisture dispersivity and satisfactory self-emulsification.

BRIEF DESCRIPTION OF THE DRAWINGS

FIGS. 1A and 1B are a table showing compositions of cleansing oils comprising a polyvalent alcohol fatty acid ester and the results of an evaluation thereof (examples); and, FIGS. 2A and 2B are a table showing the compositions of cleansing oils comprising a polyvalent alcohol fatty acid ester and the results of an evaluation thereof (comparative examples).

PREFERRED EMBODIMENTS OF THE INVENTION

A fatty acid having 6 to 12 carbon atoms used in the present invention refers to a linear or side chain, saturated or unsaturated fatty acid, preferable examples of which include caprylic acid (n-octanoic acid) and capric acid (n-decanoic acid). Fatty acids having 5 or fewer carbon atoms have safety problems such as skin irritation, while fatty acids having 13 or more carbon atoms have low ability to solubilize water. Although examples of polyvalent alcohols having 2 to 4 hydroxyl groups include propylene glycol, glycerin, diglycerin, 1,3-butylene glycol, isoprene glycol, dipropylene glycol, polyethylene glycol, pentaerythritol, neopentyl glycol and sorbitan, one or more types selected from the group consisting of glycerin, diglycerin, sorbitan and pentaerythritol are used preferably. In the case of polyvalent alcohols having 5 or more hydroxyl groups, solubility with other nonionic surfactants and oily agents becomes poor. Examples of methods for producing a polyvalent alcohol fatty acid ester of the present invention include an esterification reaction between a polyvalent alcohol and a fatty acid, a transesterification reaction between a polyvalent alcohol and a fatty acid ester, and a transesterification reaction between a polyvalent alcohol and an oil. In addition, although a polyvalent alcohol fatty acid ester can also be obtained without using polyvalent alcohol by, for example, an addition polymerization reaction of an oxirane compound to a fatty acid, a polyvalent alcohol fatty acid ester used in the present invention may be obtained by any synthesis method. A polyvalent alcohol fatty acid ester is obtained by distillation purification, decolorization treatment as necessary or, depending on the case, incorporation of two or more types of polyvalent alcohol fatty acid esters. The total amount of monoester and diester in a polyvalent alcohol fatty acid ester of the present invention is preferably 50% or more, and more preferably 60% or more. If the total amount of monoester and diester is less than 50%, the water solubilization rate becomes poor, thereby making this undesirable. In addition, the weight ratio of monoester to diester in a polyvalent alcohol fatty acid ester of the present invention is preferably 4 or less, more preferably 2.3 to 0.4, and even more preferably 1.5 to 0.4. If the weight ratio of monoester to diester is greater than 4, it becomes difficult to form a microemulsion in the presence of water, thereby causing the problem of decreased cleansing strength in the case of wet skin. Furthermore, the formation of a microemulsion can be confirmed by, for example, weighing out 10 g of a water-free cosmetic composition of the present invention at room temperature into a test tube, stirring while adding water, designating the time at which the system loses transparency as the endpoint, and calculating the water solubilization rate using the calculation formula indicated below. This solubilization rate may be 10% or more, preferably 30% or more, and more preferably 50% or more.

Solubilization rate (%) Amount of water added (g)/
[10+amount of water added (g)]×100

The amount of polyvalent alcohol fatty acid ester incorporated in a cosmetic composition of the present invention is preferably 0.1 to 80% by weight, more preferably 1 to 50% by weight, and more preferably 2 to 30% by weight, in terms of facilitating mixing with old makeup.

A nonionic surfactant used in the present invention refers to a surfactant which does not have a group which ionizes as a hydrophilic group, examples of which include those having a polyoxyalkylene group such as polyoxyethylene alkyl ether, and glycerin fatty acid esters, polyglycerin fatty acid esters, fatty acid polyalkylene glycols, sorbitan fatty acid esters, sucrose fatty acid esters, pentaerythritol fatty acid esters, fatty acid alkanol amides, ethers of polyoxyalkylene glycols and monovalent or polyvalent alcohols, polyoxyalkylene sugar ethers, condensation products of aliphatic amines and polyoxyalkylene glycols, and alkyl or alkenyl polyglycosides.

Among these nonionic surfactants, those having a polyglycerin or polyoxyalkylene group (number of carbons of alkylene chain: 2 to 4, average number of added moles: 1 to 80) are preferable, polyglycerins having an average degree of polymerization of 3 to less than 100 are particularly preferable, and polyglycerins having an average degree of polymerization of 10 to 50 are more preferable. The ring content in the polyglycerin is preferably 30% or less, and more preferably 20% or less. The ring content can be easily analyzed using EC/MS and so forth. In addition, one or more of either saturated or unsaturated fatty acid in which the number of carbons of the fatty acid is 12 to 22 is used preferably. A polyglycerin fatty acid ester can not only be used alone, but two or more types having different degrees of glycerin polymerization or different fatty acids or degrees of esterification can also be suitably used in combination.

A nonionic surfactant is incorporated into a cosmetic composition of the present invention preferably at 0.1 to 80% by weight, more preferably at 1 to 40% by weight, and even more preferably at 2 to 30% by weight in terms of cleansing strength and rinsing. In addition, a nonionic surfactant can not only be used alone, but rather two or more types having different HLB can also be suitably used in combination.

Although there are no particular limitations on the ratio between the polyvalent alcohol fatty acid ester and the nonionic surfactant in the present invention, it is preferably 15/1 to 1/15, more preferably 10/1 to 1/10, and even more preferably 1/1 to 1/5.

An oily component used in the present invention refers to that having for a main component thereof an oil in the form of a liquid and/or paste at room temperature (here, referring to a range of 15 to 25° C.) which can be used in cosmetics, examples of which include natural animal and plant oils as well as semi-synthetic oils, hydrocarbon oils, higher fatty acids, ester oils, glyceride oils, silicone oils, plant, animal and synthetic essential oil components and lipid-soluble vitamins.

Specific examples of natural plant and animal oils and semi-synthetic oils include avocado oil, linseed oil, almond oil, olive oil, wheat germ oil, sesame oil, rice germ oil, rice bran oil, safflower oil, soybean oil, primrose oil, corn oil, rapeseed oil, horse fat, palm oil, palm kernel oil, castor oil, sunflower oil, jojoba oil, macadamia nut oil, coconut oil, hydrogenated coconut oil, peanut oil and lanolin.

Examples of hydrocarbon oils include squalane, squalene, liquid paraffin and Vaseline, and examples of ester oils include diisobutyl adipate, 2-hexyldecyl adipate, 2-heptylundecyl adipate, isostearyl isostearate, trimlethylolpropane triisostearate, cetyl 2-ethylhexanoate, neopentylglycol di-2-ethylhexanoate, trimethylolpropane tri-2-ethylhexanoate, pentaerythritol tetra-2-ethylhexanoate, cetyl octanoate, oleyl oleate, octyldodecyl oleate, decyl oleate, neopentylglycol dicaprate, 2-ethylhexyl succinate, isocetyl stearate, butyl stearate, diisopropyl sebacate, cetyl lactate, tetradecyl lactate, 2-ethylhexyl palmitate, 2-hexyldecyl palmitate, 2-heptylundecyl palmitate, cholesteryl 12-hydroxystearate, phytosteryl oleate, diisostearyl malate, para-methoxycinnamic acid ester and pentaerythrite tetrarosinate.

Examples of glyceride oils include glyceryl triisostearate, glyceryl triisopalmitate, glyceryl tri-2-ethylhexanoate, glyceryl tritetradecanoate and glyceryl diparamethoxycinnamate-monoisooctylate. Examples of silicone oils include dimethyl polysiloxane, methylphenyl polysiloxane, methylhydrogen polysiloxane, octamethyl cyclopentasiloxaner decamethyl cyclohexasiloxane, higher alkoxy-modified silicones such as stearoxysilicone, alkyl-modified silicones, higher fatty acid-modified silicones and lipid-soluble vitamins such as tocopherol and derivatives thereof and retinol and derivatives thereof.

The oily component used in the present invention is not limited to the specific examples described above. In addition, solid oily components can also be incorporated provided they are of a degree which does not have an effect on retention of a liquid state.

A cosmetic composition of the present invention is able to maintain performance without impairing cleansing strength and mixing with makeup not only in a water-free non-aqueous composition, but also if water is contained. In this case, the mixing ratio of the surfactant-containing composition and oil in terms of weight ratio is preferably 10:0.1 to 0.1:10. In addition, the water content is 0 to 80% by weight, and preferably 1 to 50% by weight.

The present invention is a cosmetic composition essentially containing the aforementioned components, and can also be applied in the form of a transparent to semi-transparent, and liquid to viscous cosmetic composition capable of incorporating inorganic salts such as sodium chloride or magnesium chloride and oily gelling agents such as organic modified bentonite, hydrophobic silicic acid, silicic anhydride or starch fatty acid esters as necessary to adjust viscosity.

The present invention can suitably incorporate commonly used lower alcohols, powders, functional beads, capsules, antioxidants, ultraviolet absorbers, plant extracts, moisture retention agents, bactericides, anti-inflammatory agents, preservatives, pigments, fragrances and so forth in addition to the aforementioned components.

There are no particular limitations on cosmetics containing a cosmetic composition of the present invention, and examples of which include cleansing cosmetics for oily cosmetics, shampoos, scalp cleansers, bathing cosmetics, milky liquids and beauty washes, with applications in the form of cleansing cosmetics and bathing cosmetics being preferable.

EXAMPLES

Effects of the present invention were evaluated according to the methods described below.
1. Solubilization Rate (Confirmation of Microemulsion Formation)

10 g of a test composition were weighed out into a test tube at room temperature followed by stirring while adding water thereto and designating the time at which the system loses transparency as the endpoint. The solubilization rate was then calculated using the calculation formula indicated below.

Solubilization rate (%)=Amount of water added (g)/
[10+amount of water added (g)]×100

2. Cleansing Test (when not Wet)

After applying lipstick to the forearm over an area measuring 2 cm×2 cm and allowing to stand for 30 minutes, 0.5 g of a test composition were massaged so as to remove the lipstick for 30 seconds followed by rinsing off with water. The degree of lipstick removal was then evaluated visually according to the criteria indicated below.

A: Completely removed
B: Nearly completely removed
C: Not removed very well
D: Not removed at all 3. Cleansing Test (when Wet)

After applying lipstick to the forearm over an area measuring 2 cm×2 cm and allowing to stand for 30 minutes, the arm was dampened with water and 0.5 g of a test composition were massaged so as to remove the lipstick for 30 seconds followed by rinsing off with water. The degree of lipstick removal was then evaluated visually according to the criteria indicated below.

A: Completely removed
B: Nearly completely removed
C: Not removed very well
D: Not removed at all 4. Usage Test Ten panelists wearing makeup placed 1 g of a test composition in their hand, applied the test composition to the face with both hands, massaged for 30 seconds and then rinsed the composition off with water followed by making a sensory evaluation of "ease of mixing into old makeup", "ease of rinsing" and "oily sensation during rinsing". Evaluations were made to one of five ranks consisting of 1 (poor or present) to 5 (good or absent), an average score of 4.5 or more was evaluated as A, 4 or more as B, 3 to less than 4 as C, and less than 3 as D.

Examples 1-13 and Comparative Examples 1-10

The evaluation results for cleansing oils containing a polyvalent alcohol fatty acid ester produced in accordance with ordinary methods are shown in FIGS. 1A and 1B and FIGS. 2A and 2B.

As is clear from FIGS. 1A and 1B and FIGS. 2A and 2B, the cleansing oils of the present invention all mixed well with old makeup, demonstrated superior cleansing strength, and did not leave an oily sensation.

INDUSTRIAL APPLICABILITY

A cosmetic composition and cosmetics of the present invention can be used in cleansing cosmetics demonstrating superior cleansing strength even if the skin is wet which mix well with old makeup, and in bathing cosmetics having superior moisture dispersivity and satisfactory self-emulsification.

The invention claimed is:

1. A cosmetic composition comprising: a nonionic surfactant; and a polyvalent alcohol fatty acid ester of a fatty acid having 6 to 12 carbon atoms and a polyvalent alcohol having 2 to 4 hydroxyl groups; wherein, a total amount of monoester and diester in the polyvalent alcohol fatty acid ester is 50% or more, and a weight ratio of monoester to diester is 4 or less, the nonionic surfactant is a polyglycerin fatty acid ester, an average degree of polymerization of a constituent polyglycerin of the polyglycerin fatty acid ester is from 3 to less than 100, and a content of a cyclic form is 30% or less of the constituent polyglycerin.

2. The cosmetic composition according to claim 1, containing an oil which is in the form of a liquid and/or paste at room temperature.

3. The cosmetic composition according to claim 1 or 2, wherein the polyvalent alcohol having 2 to 4 hydroxyl groups is one or more types selected from the group consisting of glycerin, diglycerin, sorbitan and pentaerythritol.

4. The cosmetic composition according to claim 1, wherein a water content in the cosmetic composition is 0 to 80% by weight.

5. The cosmetic composition according to claim 1, wherein the cosmetic composition is a cleansing cosmetic composition or a bathing cosmetic composition.

6. A cosmetic containing the cosmetic composition according to claim 1.

7. The cosmetic composition according to claim 1, wherein the fatty acid has 6 to 10 carbon atoms.

8. The cosmetic composition according to claim 1, wherein the fatty acid has 8 to 10 carbon atoms.

* * * * *